(12) United States Patent
Parastegari et al.

(10) Patent No.: US 12,082,902 B2
(45) Date of Patent: Sep. 10, 2024

(54) HEAD MOVEMENT CONTROL OF A VIEWING SYSTEM

(71) Applicant: Intuitive Surgical Operations, Inc., Sunnyvale, CA (US)

(72) Inventors: Sina Parastegari, Campbell, CA (US); Goran Lynch, Oakland, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 381 days.

(21) Appl. No.: 17/637,060

(22) PCT Filed: Aug. 21, 2020

(86) PCT No.: PCT/US2020/047493
§ 371 (c)(1),
(2) Date: Feb. 21, 2022

(87) PCT Pub. No.: WO2021/041248
PCT Pub. Date: Mar. 4, 2021

(65) Prior Publication Data
US 2022/0287788 A1 Sep. 15, 2022

Related U.S. Application Data

(60) Provisional application No. 62/891,229, filed on Aug. 23, 2019.

(51) Int. Cl.
A61B 34/00 (2016.01)
A61B 34/37 (2016.01)
(Continued)

(52) U.S. Cl.
CPC .............. *A61B 34/77* (2016.02); *A61B 34/25* (2016.02); *A61B 34/37* (2016.02); *B25J 9/1689* (2013.01);
(Continued)

(58) Field of Classification Search
CPC ......... A61B 34/77; A61B 34/25; A61B 34/37; A61B 2017/00216; A61B 2034/2059;
(Continued)

(56) References Cited

U.S. PATENT DOCUMENTS 10,335,572 B1 * 7/2019 Kumar .................... G06F 3/015
2018/0092706 A1 * 4/2018 Anderson .............. A61B 34/30
(Continued)

FOREIGN PATENT DOCUMENTS

CA 3035251 A1 3/2018
WO 0195319 A1 10/2018

OTHER PUBLICATIONS

International Search Report issued in corresponding international application No. PCT/US2020/047493 mailed Nov. 12, 2020 (4 pages).

(Continued)

Primary Examiner — Jaime Figueroa
Assistant Examiner — Sihar A Karwan
(74) Attorney, Agent, or Firm — Osha Bergman Watanabe & Burton LLP

(57) ABSTRACT

A computer-assisted medical system includes a display unit configured to provide images to an operator of the display unit, a headrest configured to receive a mechanical input provided by a head of the operator in mechanical contact with the headrest, a headrest sensor interfacing with the headrest and configured to provide sensor signals based on the mechanical input, and a controller. The controller includes a computer processor, and is configured to process the sensor signals to obtain a driving input, drive, by the driving input, a virtual mass to obtain a simulated virtual mass movement, and cause movement of the headrest, the movement of the headrest tracking the virtual mass movement.

24 Claims, 9 Drawing Sheets

(51) Int. Cl.
  *B25J 9/16* (2006.01)
  *A61B 17/00* (2006.01)
  *A61B 34/20* (2016.01)

(52) U.S. Cl.
  CPC ............... *A61B 2017/00216* (2013.01); *A61B 2034/2059* (2016.02)

(58) Field of Classification Search
  CPC ............. A61B 34/74; A61B 2090/064; A61B 2090/066; A61B 90/60; B25J 9/1689; G05B 2219/45123
  See application file for complete search history.

(56) References Cited

U.S. PATENT DOCUMENTS

2019/0209145 A1\* 7/2019 Herzlinger ............ G06F 3/0338
2020/0038124 A1\* 2/2020 Lin ........................ A61B 34/10

OTHER PUBLICATIONS

Written Opinion of the International Searching Authority issued in corresponding international application No. PCT/US2020/047493 mailed Nov. 12, 2020 (7 pages).
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

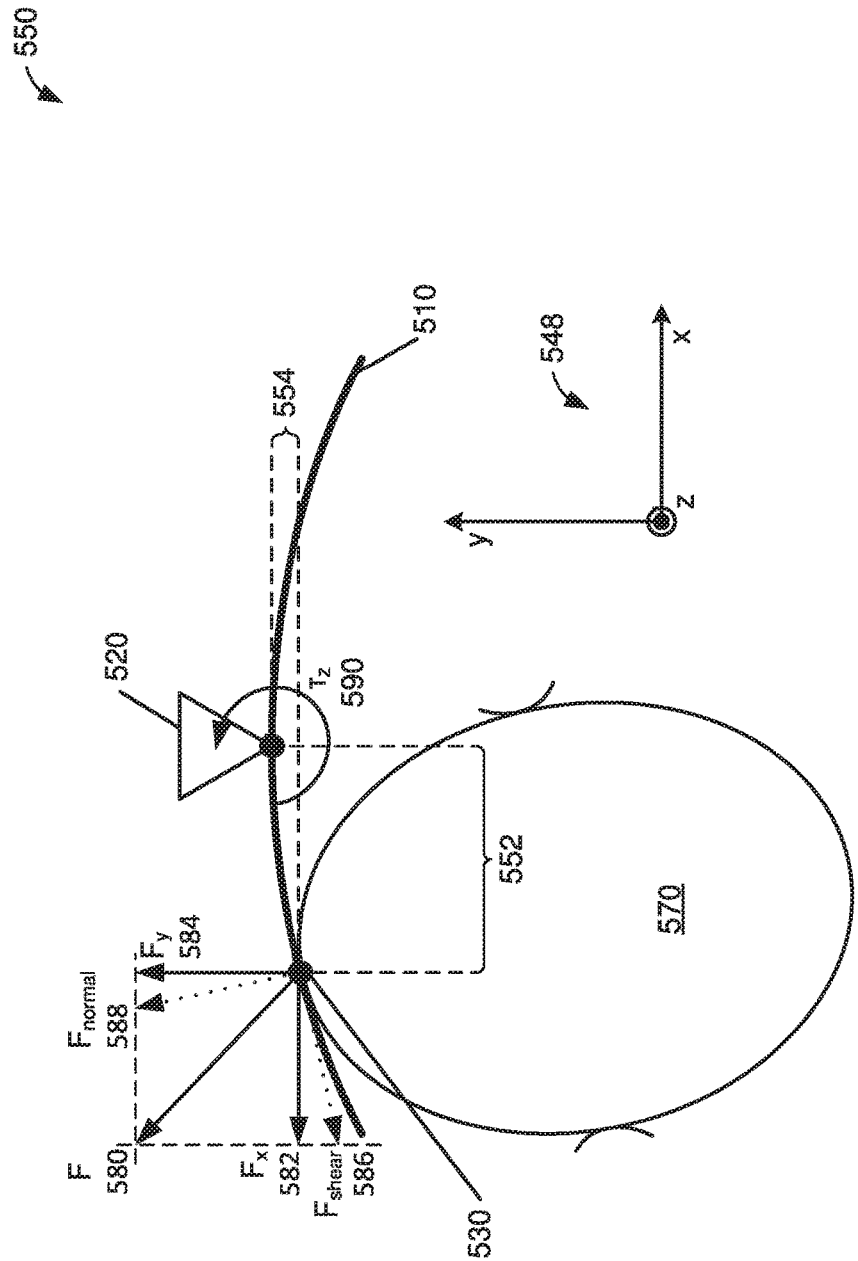

HEAD MOVEMENT CONTROL OF A VIEWING SYSTEM

CROSS-REFERENCE TO RELATED APPLICATIONS

This patent application is a U.S. national phase application of International Application No. PCT/US2020/047493, filed on Aug. 21, 2020. International Application No. PCT/US2020/047493 claims the benefit of priority under 35 U.S.C. § 119(e) to U.S. Provisional Patent Application Ser. No. 62/891,229, filed on Aug. 23, 2019. All mentioned U.S. patent applications, U.S. provisional patent applications, and international applications are incorporated by reference herein in their entirety.

BACKGROUND

Field of Invention

The present invention generally provides improved robotic and/or medical (including surgical) devices, systems, and methods.

Overview

A system of robotic devices may be used to perform a task at a worksite.

An operator may view images of the worksite, obtained by an imaging device (e.g. an endoscope, an optical camera, or an ultrasonic probe). The images may enable the operator to monitor and/or perform the task using visual feedback from the worksite, provided to the operator by a display unit.

The imaging device may be controllable to update the view of the worksite. The imaging device may be attached to a robotic manipulator and the robotic manipulator may include two or more links coupled together by one or more joints. The joints may be moved to update the position and/or orientation of the imaging device at the worksite. The movement of the imaging device may be controlled by the operator, enabling the operator to change the view of the worksite as necessary or desired for performing the task.

Robotic systems equipped with display units that provide visual feedback to the operator include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures may include a remotely controllable robotic manipulator. One or more robotic manipulators may be equipped with an imaging device to provide visual feedback to the operator via the display unit. Operators may remotely control motion of the one or more remotely controllable robotic manipulators.

SUMMARY

In general, in one aspect, one or more embodiments relate to a computer-assisted medical system comprising: a display unit configured to provide images to an operator of the display unit; a headrest configured to receive a mechanical input provided by a head of the operator in mechanical contact with the headrest; a headrest sensor interfacing with the headrest and configured to provide sensor signals based on the mechanical input; a controller comprising a computer processor, the controller configured to: process the sensor signals to obtain a driving input; drive, by the driving input, a virtual mass to obtain a simulated virtual mass movement; and cause movement of the headrest, the movement of the headrest tracking the virtual mass movement.

In general, in one aspect, one or more embodiments relate to a method for operating a medical system. The method comprises obtaining sensor signals from a headrest sensor, wherein the headrest sensor interfaces with a headrest configured to receive a mechanical input provided by a head of an operator, the head being in mechanical contact with the headrest, and wherein the sensor signals are based on the mechanical input; processing the sensor signals to obtain a driving input; driving, by the driving input, a virtual mass to obtain a simulated virtual mass movement; and causing movement of the headrest, the movement of the headrest tracking the virtual mass movement.

In general, in one aspect, one or more embodiments relate to non-transitory machine-readable medium comprising a plurality of machine-readable instructions executed by one or more processors associated with a medical system, the plurality of machine-readable instructions causing the one or more processors to perform a method comprising: obtaining sensor signals from a headrest sensor, wherein the headrest sensor interfaces with a headrest configured to receive a mechanical input provided by a head of an operator, the head being in mechanical contact with the headrest, and wherein the sensor signals are based on the mechanical input; processing the sensor signals to obtain a driving input; driving, by the driving input, a virtual mass to obtain a simulated virtual mass movement; and causing movement of the headrest, the movement of the headrest tracking the virtual mass movement.

Other aspects of the invention will be apparent from the following description and the appended claims.

BRIEF DESCRIPTION OF DRAWINGS

FIGS. 5A and 5B show interactions of an operator's head with a head input device of the display unit, in accordance with one or more embodiments.

DETAILED DESCRIPTION

Figure 1:
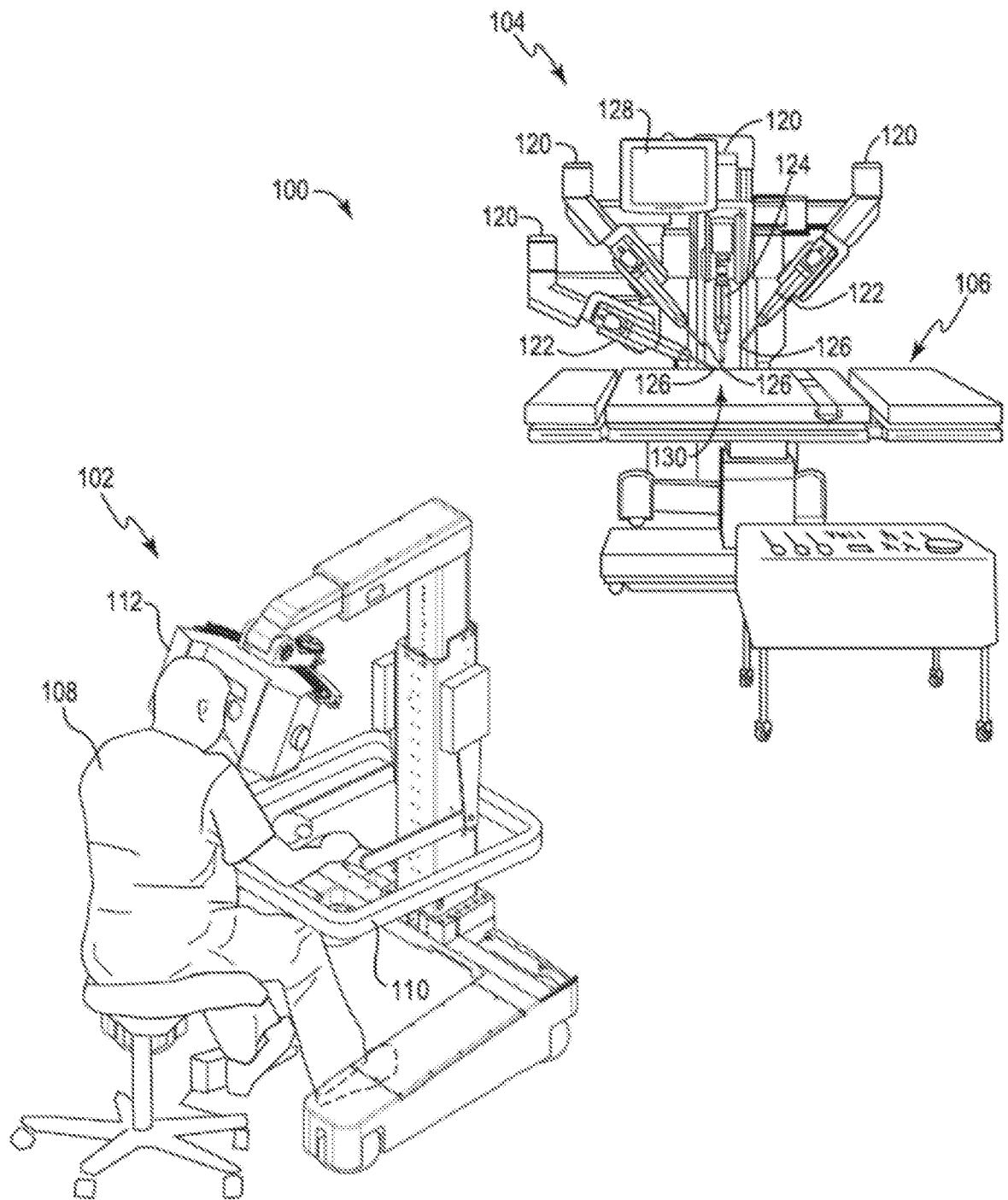
FIG. 1 shows an example teleoperated surgical system in accordance with one or more embodiments.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques may also be used for medical treatment or diagnosis procedures that do, or do not, include surgical aspects.

In general, embodiments of the disclosure may facilitate the use of robotic systems and improve the workflow under various conditions. A robotic system may include an imaging device, enabling an operator to view a worksite. The position and/or orientation of the imaging device may be controllable by the operator. In one or more embodiments of the disclosure, the operator uses head movements to control movement of the imaging device. The operator's head may be in contact with a headrest, and head movement may be registered by a headrest sensor coupled to the headrest. The signals obtained from the headrest sensor may be used to update the position and/or orientation of the imaging device. Assuming a stationary display unit displaying the images from the imaging to the operator, the operator's head movement would result in a misalignment between the operator's eyes and the display unit. Such a misalignment would degrade the visual information available to the operator, in particular when stereoscopic visual information is provided by the display unit. Accordingly, in one or more embodiments, head movement of the operator causes a compensatory movement of the display unit, thereby resulting in the display unit to remain in alignment with the operator's eyes. The compensatory movement may be performed under consideration of the human anatomy, thereby ensuring an ergonomic and effortless control while avoiding fatigue of the operator.

Referring now to the drawings, in which like reference numerals represent like parts throughout the several views, FIG. 1 is a diagrammatic view of an example teleoperated system (100), which may be used with one or more features disclosed herein, and which may be a surgical system. As shown, the teleoperated system (100) may include a master control subsystem, which may be in the form of a workstation (e.g., console) (102), and a slave device (104).

In this example, the master control workstation (102) includes one or more master control devices which are contacted and manipulated by the operator's hands, e.g., one master control device for each hand. The master control devices are supported by the workstation (102) and may be mechanically grounded. An ergonomic support (110) (e.g., forearm rest) may be provided in some implementations, on which the operator (108) may rest his or her forearms while grasping the master control devices. In some examples, the operator (108) may perform tasks at a work site near the slave device (104) during a medical procedure by controlling the slave device (104) using the master control devices.

A display unit (112) is included in the workstation (102). The display unit (112) may display images for viewing by the operator (108). The display unit (112) may be moved in various degrees of freedom to accommodate the operator's viewing position and/or to provide control functions. In the example of the teleoperated system (100), displayed images may depict a work site at which the operator is performing various tasks via control of the master control devices. In some examples, the images displayed by the display unit (112) may be received by the workstation (102) from one or more image capture devices arranged at a remote work site. In other examples, the images displayed by the display unit may be generated by the display unit (or by a connected other device or system), such as for virtual representations of tools, the worksite, or for user interface components.

When using the workstation (102), the operator (108) may sit in a chair or other support in front of the workstation (102), position his or her eyes in front of the display unit (112), grasp and manipulate the master control devices, and rest his or her forearms on the ergonomic support (110) as desired. In some implementations, the operator may stand at the workstation or assume other poses, and the display unit (112) and master control devices may be adjusted in position (height, depth, etc.) to accommodate.

The teleoperated system (100) may also include slave device (104) which may be controlled by the master control workstation (102). In a medical example, the slave device (104) is located near an operating table (106) (e.g., table, bed, or other support) on which a patient may be positioned. A work site (130) may be provided on the operating table (106), e.g., on or in a patient, simulated patient or model, etc. (not shown). The teleoperated slave device (104) shown includes a plurality of manipulator arms (120), each configured to couple to an instrument assembly (122). An instrument assembly (122) may include, for example, an instrument (126) and an instrument carriage (not shown) configured to hold the instrument (126).

In various implementations, one or more of the instruments (126) may include image capture devices (e.g., cameras), such as a camera included in an endoscope assembly (124), which may provide captured images of a portion of the work site to be displayed by the display unit (112) of the workstation (102) for output.

In some implementations, the slave manipulator arms (120) and/or instrument assemblies (122) may be controlled to move and articulate the instruments (126) in response to manipulation of master control devices by the operator (108), so that the operator (108) may perform tasks at the work site (130). For a surgical example, the operator may direct surgical procedures at internal surgical sites through minimally invasive surgical apertures.

In some implementations, a control system is provided in master control workstation (102) or is provided externally to the workstation (102) and communicates with the workstation (102). As the operator (108) moves master control device(s), sensed spatial information and sensed orientation information is provided to the control system based on the movement of the master control devices. The control system may determine or provide control signals to the slave device (104) to control the movement of the arms (120), instrument assemblies (122), and instruments (126) based on the received information and user input. In one embodiment, the control system supports one or more wireless communication protocols such as Bluetooth, IrDA, HomeRF, IEEE 802.11, DECT, and Wireless Telemetry.

Continuing with FIG. 1, the control system may be implemented on one or more computing systems (not shown). One or more computing systems may be used to control the slave device (104). In addition, one or more computing systems may be used to control components of the master control workstation (102), such as movement of a display unit (112) in response to an operator's head movement.

A computing system may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system may be an integrated circuit for processing instructions. For example, the computer processor may be one or more cores or micro-cores of a processor. The computing system may also include one or more input devices, such as a touchscreen, keyboard, mouse, microphone, touchpad, electronic pen, or any other type of input device.

A communication interface of a computing system may include an integrated circuit for connecting the computing system to a network (not shown) (e.g., a local area network (LAN), a wide area network (WAN) such as the Internet, mobile network, or any other type of network) and/or to another device, such as another computing system.

Further, the computing system may include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

Continuing with FIG. 1, a computing system may be connected to or be a part of a network. The network may include multiple nodes. Each node may correspond to a computing system, or a group of nodes. By way of an example, embodiments of the disclosure may be implemented on a node of a distributed system that is connected to other nodes. By way of another example, embodiments of the invention may be implemented on a distributed computing system having multiple nodes, where each portion of the disclosure may be located on a different node within the distributed computing system. Further, one or more elements of the aforementioned computing system may be located at a remote location and connected to the other elements over a network.

In some implementations, the display unit (112) may be operated by an operator in conjunction with the operation of one or more ungrounded master control devices (ungrounded master control devices being not kinematically grounded, such as master control devices held by the operator's hands without additional physical support). In some implementations, the operator may use display unit (112) that is positioned near to the work site such that the operator may manually operate instruments at the work site, such as a laparoscopic instrument in a surgical example, while viewing images displayed by the display unit (112).

Some implementations may include one or more components of a teleoperated medical system such as a da Vinci® Surgical System, commercialized by Intuitive Surgical, Inc. of Sunnyvale, California, U.S.A. Implementations on da Vinci® Surgical Systems are merely examples and are not to be considered as limiting the scope of the features disclosed herein. For example, different types of teleoperated systems having slave devices at work sites, as well as non-teleoperated systems, may make use of features described herein.

Figure 2:
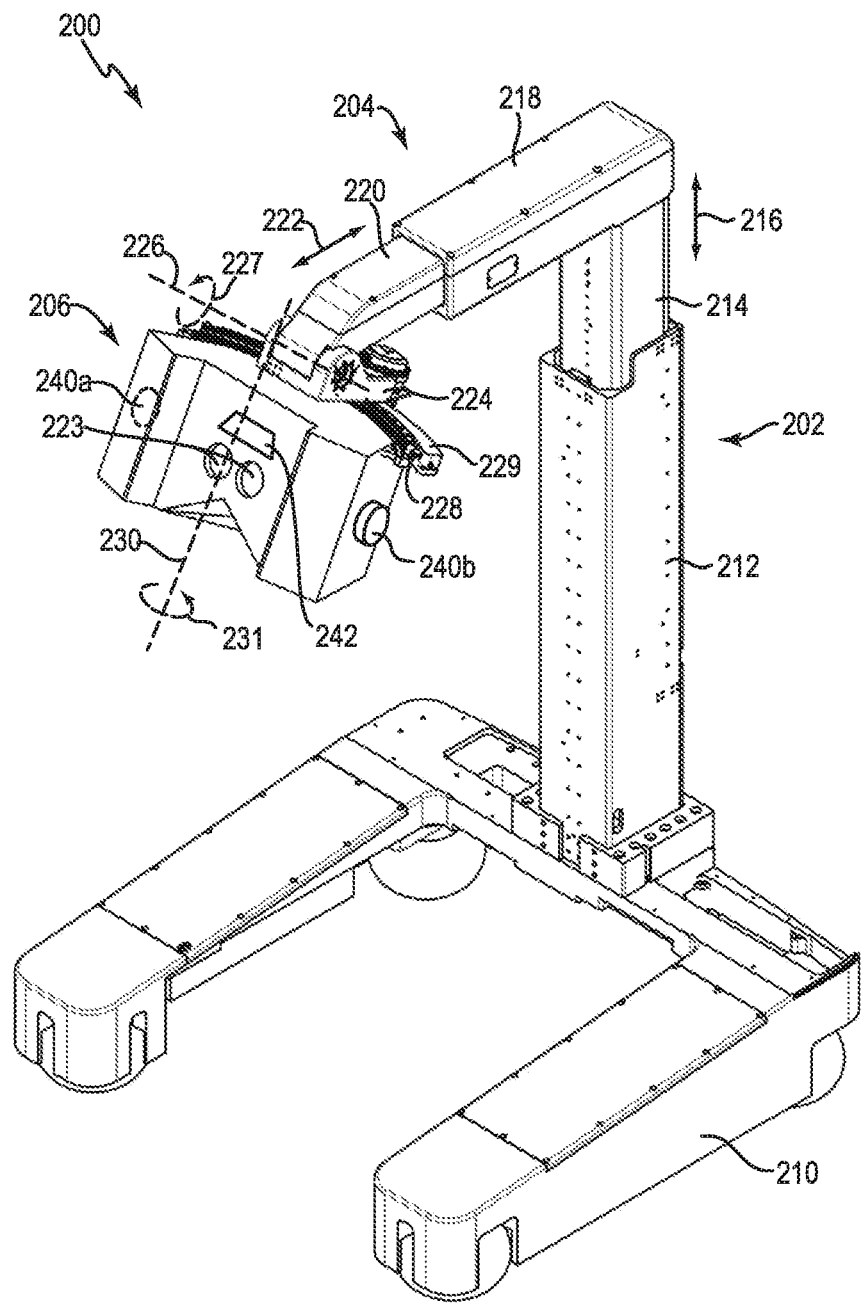
FIG. 2 shows a display system in accordance with one or more embodiments.

FIG. 2 is a perspective view of an example display system (200), in accordance with one or more embodiments. In one or more embodiments, the display system (200) is used in a master control workstation of a teleoperated system (e.g., in a master control workstation (102) of the teleoperated system (100) of FIG. 1), or may be used in other systems or as a standalone system, e.g., to allow an operator to view a work site or other physical site, a displayed virtual environment, etc.

The display system (200) includes a base support (202), an arm support (204), and a display unit (206). As described in greater detail below, the display unit (206) is provided with multiple degrees of freedom of movement provided by a support linkage including base support (202), arm support (204) coupled to the base support (202), and a tilt member (224) (described below) coupled to the arm support (204), where the display unit (206) is coupled to the tilt member.

The base support (202), may be a vertical member that is mechanically grounded, e.g., directly or indirectly coupled to ground. For example, the base support (202) may be mechanically coupled to a support structure (210) that is coupled to the ground to provide stability to the base support (202). The base support (202) includes a first base portion (212) and a second base portion (214) coupled such that the second base portion (214) is translatable with respect to the first base portion (212) in a linear degree of freedom. Other implementations may use different configurations.

The arm support (204) may be a horizontal member that is mechanically coupled to the base support (202). The arm support (204) includes a first arm portion (218) and a second arm portion (220). The second arm portion (220) is a distal portion of the arm support (204) coupled to the first arm portion (218) such that the second arm portion (220) is linearly translatable with respect to the first arm portion (218). Other implementations may use different configurations.

In other implementations, the arm support (204) may extend at various heights and/or configurations, e.g., below an operator's head or body, at the height of the operator's head, in back of operator and yoking around an operator, etc.

Continuing with FIG. 2, the display unit (206) may be mechanically coupled to the arm support (204). The display unit (206) may be moveable in two linear degrees of freedom provided by the linear translation of the second base portion (214) and second arm portion (220).

In one or more embodiments, the display unit (206) includes a display device, e.g., one or more display screens, projectors, or other display devices, that may display digital images. The display unit (206) may include two viewports (223), where the display device is provided behind or included in the viewports. One or more display screens or other display devices may be positioned on the display unit (206) in place of the viewports (223).

In one or more embodiments, the display unit (206) displays images of a surgical site, captured by an imaging device such as an endoscope. The surgical site may alternatively be a virtual representation of a surgical site. The images may show captured images or virtual renderings of instruments (126) of the slave device (104) while one or more of these instruments are controlled by the operator via the master control devices of the master control workstation (102). The images may further include information such as status information, alerts and warnings, notifications, etc. Such information may be displayed in combination with a view of a work site, or without a work site view.

In one or more embodiments, the display unit (206) is rotationally coupled to the arm support (204) by a tilt member (224). In this example, the tilt member (224) is coupled at a first end to the second arm portion (220) of the arm support (204) by a rotary coupling configured to provide rotational motion of the tilt member (224) and the display unit (206) about the tilt axis (226) with respect to the second arm portion (220). In one or more embodiments, the tilt axis (226) is be positioned above the display device in the display unit (206). In one or more embodiments, the tilt axis (226) is positioned above a position of an operator's head when the operator operates the display unit (206).

Continuing with FIG. 2, each of the various degrees of freedom discussed herein may be passive and require manual manipulation, or be movable by one or more actuators, such as by one or more motors, solenoids, etc. For example, the rotational motion of the tilt member (224) and the display unit (206) about the axis (226) may be driven by one or more actuators, such as a motor coupled to the tilt member at or near the tilt axis (226). The base support (202), arm support (204), and tilt member (224) may be considered to be a support linkage having the display unit (206) coupled at the distal end of the support linkage.

The display unit (206) may be rotationally coupled to the tilt member (224) and may rotate about a yaw axis (230). For example, this may be lateral or left-right rotation from the point of view of an operator viewing images of the display unit (206) via the viewports (223). In this example, the display unit (206) is coupled to the tilt member by a rotary mechanism which may be a track mechanism. For example, in some implementations, the track mechanism includes a curved track (228) that slidably engages a groove member (229) coupled to the tilt member (224), allowing the display unit (206) to rotate about the yaw axis (230) by moving curved track (228) through a groove of the groove member (229). In some implementations, a curved track is coupled to tilt member (224) and a groove member is coupled to display unit (206). In some implementations, the curved track (228) may be a curved cam follower that engages a cam roller.

The curvature (e.g., radius) of the curved track (228) and/or groove member provides the yaw axis (230) at a particular distance from an operator side of the display unit (206) and/or from the tilt axis (226). For example, this may be a particular horizontal distance that is parallel to the degree of freedom (222) of the second arm portion (220). For example, the yaw axis (230) may be provided at a distance such that it approximately intersects a defined (e.g., virtual or software-defined) neck pivot axis corresponding to a pivot axis in an operator's neck. The defined neck pivot axis may be used as a reference for motion of the display unit (206) in some implementations.

Continuing with FIG. 2, the display system (200) may thus provide the display unit (206) with a vertical linear degree of freedom (216), a horizontal linear degree of freedom (222), a rotational (tilt) degree of freedom (227), and a rotational yaw degree of freedom (231). A combination of coordinated movement of components of the display system (200) in these degrees of freedom allow the display unit (206) to be positioned at various positions and orientations in its workspace. The motion of the display unit (206) in the tilt, horizontal, and vertical degrees of freedom allows the display unit (206) to stay close to the operator's head and eyes during operator head motion, and/or maintain a physical connection between the operator's head (e.g., forehead) and the display unit (206).

For example, the display unit (206) is positionable (e.g., translatable and/or rotatable) in its workspace such that eyes of the operator align with the viewports of the display unit. In addition, the display unit (206) may be rotated in physical space about a defined eye pivot axis corresponding to, for example, an eye axis through both of an operator's eyes to allow a desired vertical (e.g., up-down) eye viewing angle and a desired yaw (e.g., left-right) viewing angle for the operator.

The degrees of freedom of the display system allow the display system (200) to provide pivoting motion of the display unit (206) in physical space about a pivot axis that may be positioned in different locations. For example, the system (200) may provide motion of the display unit (206) in physical space that corresponds to motion of an operator's head when operating the display system (200). This motion may include rotation about a defined neck pivot axis that approximately corresponds to a neck axis of the operator's head at the operator's neck. This rotation allows the display unit (206) to be moved in accordance with the operator's head that is directing movement of the display unit (206). In another example, the motion may include rotation about a defined forehead pivot axis that approximately corresponds to a forehead axis extending through the operator's head at the forehead when the display unit (206) is oriented, as shown, in a centered yaw rotary position about the yaw axis (230).

Display unit (206) may include input devices that allow an operator to provide input to manipulate the orientation and/or position of the display unit (206) in space, and/or to manipulate other functions or components of the display system (200) and/or a larger system (e.g., teleoperated system).

The display unit (206) may include a head input device (242). In one or more embodiments, the head input device (242) is positioned on a surface of the display unit (206) that is facing the operator's head during operation of the display unit (206).

The head input device (242) may be shaped to form a headrest which may be in contact with the operator's head. More specifically, the head input device (242) may be located in a region above the viewports (223) to be in contact with the operator's forehead while the operator is viewing images through the viewports (223). The head input device (242) may include one or more head input sensors that sense operator head input that is received as commands to cause movement of the imaging device, thereby updating the view in the images presented to the operator. Further, in one or more embodiments, the sensed head movement is used to move the display unit (206) to compensate for the head movement. The operator's head position may, thus, remain stationary relative to the viewports (223), even when the operator performs head movements to control the view provided by the imaging device. A proper alignment of the operator's eyes with the viewports may thus be ensured.

In one or more embodiments, sensing the operator head input includes sensing a presence or contact by an operator's head or portion of the head (e.g., forehead) with the head input device (242). The one or more head input sensors may include any of a variety of types of sensors, e.g., resistance sensors, capacitive sensors, force sensors, optical sensors, etc.

Continuing with FIG. 2, the orientation and/or position of the display unit (206) may be changed by the display system (200) based on the operator head input to head input device (242). For example, sensed operator input is provided to a control system, which controls actuators of the display system (200) to move the second base portion (214) in linear degree of freedom (216), the second arm portion (220) in linear degree of freedom (222), tilt member (224) in rotary degree of freedom (227), and/or display unit (206) in rotary degree of freedom (231), to cause the display unit (206) to be moved as commanded by (e.g., in accordance with) the sensed operator head input. Sensed operator head input may also be used to control other functions of the display system (200) and/or of a larger system (e.g., teleoperated system 100 of FIG. 1). Thus, in some implementations, the operator may move his or her head to provide input to input device to control the display unit (206) to be moved by the display system in accordance with the motion of the head, thus allowing the display unit to follow motions of the operator's head and changes in viewing angle.

In some implementations, images displayed by the display unit (206), and/or other controlled devices, are changed and manipulated based on the sensed motion of the display unit (206).

In some implementations of a display system, the display unit (206) is rotatable about yaw axis (230) in degree of freedom (231) and one or more of the other degrees of freedom (216), (222), and (227) are omitted from the display system (200). For example, the display unit (206) may be rotated about the yaw axis (230) (e.g., by actuator(s) and/or manually by an operator) and the display unit (206) may be manually positioned higher and/or lower (e.g., by actuator(s) and/or manually by an operator), e.g., using the base support (202) or other mechanism, where horizontal degree of freedom (222) and/or tilt degree of freedom (227) are omitted.

Those skilled in the art will appreciate that FIG. 2 merely shows an example for a configuration of a display system (200). Alternative configurations supporting movement of the display unit (206) based on an operator's input to the head input device (242) may be used without departing from the disclosure. Any linkage that supports the desired movement of the display unit (206) may be used in lieu of the configuration shown in FIG. 2. A detailed description of the use of signals captured at the head input device (242) to cause movement of the display unit (206) is provided below with reference to FIGS. 3, 4, 5A, 5B, 6, 7, and 8.

Figure 3:
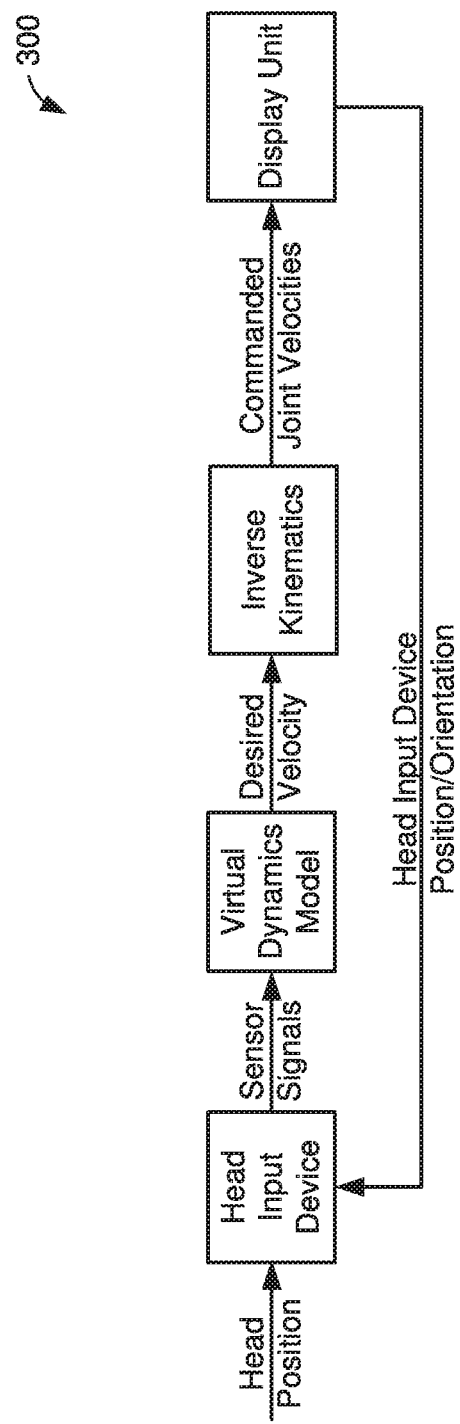
FIG. 3 shows a control architecture for controlling movement of a display unit, in accordance with one or more embodiments.

Turning to FIG. 3, a control architecture (300) for controlling movement of the display unit, in accordance with one or more embodiments of the disclosure, is shown. While FIG. 3 provides a high-level introduction to controlling movement of a display unit based on detected head movement, the subsequently discussed flowcharts provide a description of the steps that may be performed. A key aspect of the control architecture of FIG. 3 is that, in accordance with one or more embodiments of the disclosure, the dynamics of moving the display unit is decoupled from the force input provided by the operator. More specifically, the force input by the operator, is used to simulatively drive a virtual dynamics model. The display unit may then be driven to follow the virtual movement produced by the virtual dynamics model. Accordingly, assuming that the movement of the display unit mirrors the movement simulated by the virtual dynamics model, the dynamics of the display unit are transparent to the operator, and the dynamics experienced by the operator are, instead, governed by the virtual dynamics model. Accordingly, the operator's experience of how head movement causes movement of the display unit (and an updating of the view provided by the display unit) may be adjusted as desired by changing the characteristics of the virtual dynamics model.

In the control architecture of FIG. 3, the head position or a changing head position (i.e., a head movement) is considered an input acting on the head input device. Interaction of the head with the head input device results in a force acting between the head and the head input device. The force is registered by the head input sensor. Depending on the distance between the point of contact between head and head input device and the head input sensor location, the force may cause different types of sensor signals. Specifically, as subsequently illustrated in FIG. 4, various forces and/or torques in various directions may be registered for head movements in a horizontal and a vertical plane. The head input sensor signals may be used to drive the virtual dynamics model. The virtual dynamics model may include a virtual mass which may be simulatively driven by the sensor signals, resulting in an acceleration of the virtual mass. The resulting movement of the simulated mass may govern the movement of the display unit. Specifically, the velocity of the virtual mass may serve as a desired velocity input to an inverse kinematics model representing the linkage of the display unit. The output of the inverse kinematics model may be joint velocities that may be used to drive the actuators of the joints, causing movement of the display unit as specified by the simulated movement of the virtual mass. The movement of the display unit results in a change of the head input device position. In one or more embodiments the control architecture is designed to compensate for the operator's head movement. Accordingly, the control architecture may make the display unit "follow" the head movement to reduce the offset between the point of contact and the head input device center. The flowcharts, discussed below, provide details regarding possible implementations of the control architecture.

Figure 4:
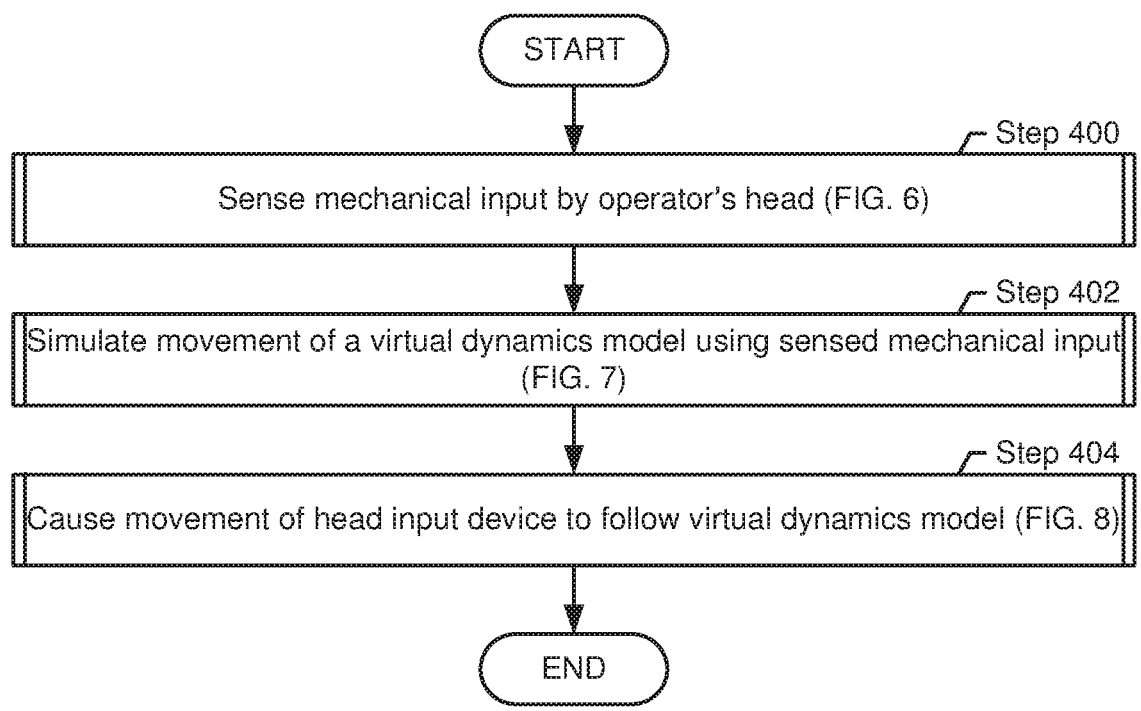
FIG. 4 shows a flowchart describing a method for head movement control of a display unit in accordance with one or more embodiments.

Turning to the flowcharts, FIG. 4 shows a flowchart in accordance with one or more embodiments. The flowchart of FIG. 4 depicts a method for controlling movement of a viewing system using head movement. The viewing system may include the previously described imaging device and the previously described display unit of a user control system. Head movement of the operator interacting with the display unit may cause movement of the imaging device. In addition, the head movement, in accordance with one or more embodiments, causes movement of the display unit to maintain alignment of the display unit with the operator's head. One or more of the steps in FIG. 4 may be performed by various components of the systems, previously described with reference to FIG. 1 and FIG. 2. These figures describe particular system configurations serving as examples. However, the subsequently described methods are not limited to a particular configuration of a system. Instead, the methods are applicable to any type of system that includes an imaging device that allows an updating of the view provided by the imaging device, paired with a movable display unit. The method of FIG. 4 may be used for head movement input in a horizontal plane and/or in a vertical plane. An additional discussion of the control in the horizontal vs the vertical plane is provided below.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 4.

Turning to the flowchart of FIG. 4, a series of steps which, when executed repeatedly, may form a loop in which movement of the operator's head is detected and causes a compensatory movement of the display unit, are shown.

Figure 5A:
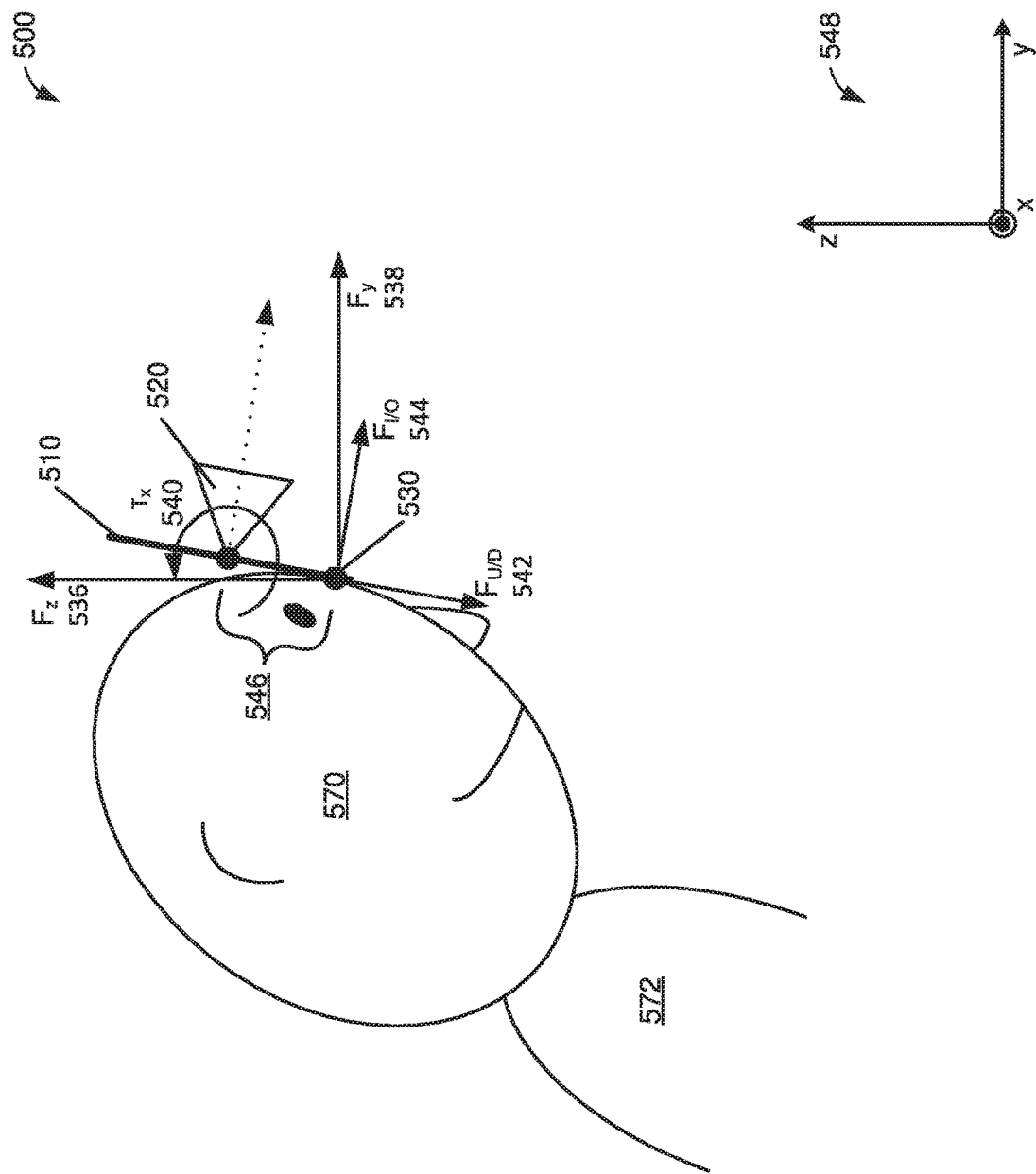

In Step 400, a mechanical input provided by the operator's head is sensed, in accordance with one or more embodiments. The sensing may be performed using the previously introduced head input sensor. The sensing may be performed in a vertical plane (as illustrated in FIG. 5A) and/or in a horizontal plane (as illustrated in FIG. 5B). Various sensor signals representing the mechanical input by the operator's head may be obtained in Step 400, using the head input sensor. A detailed description of Step 400 is provided below with reference to FIG. 6.

In Step 402, a movement is simulated using a virtual dynamics model, in accordance with one or more embodiments. The simulated movement may be driven by the sensed mechanical input obtained in Step 400. In one or more embodiments, the virtual dynamics model establishes the dynamics of the moving display unit, regardless of the mechanical configuration of the display unit. The virtual dynamics model may, thus, impose desired dynamics to be experienced by the operator when using head movements for controlling the viewing system. Accordingly, the desired dynamics may be set to satisfy various different needs. For example, one operator may prefer a highly responsive system that requires a minimum of head movement as a control input, whereas another operator may prefer a less responsive system, e.g., to achieve a particularly high precision. Such characteristics may be achieved by, for example, modulating gains applied to the sensed mechanical input, adjusting the inertia of the virtual dynamics model, etc. These and other aspects of Step 402 are discussed in detail below with reference to FIG. 7.

In Step 404, the display unit and the head input device of the display unit are caused to follow the movement of the virtual dynamics model, in accordance with one or more embodiments. Accordingly, the movement of the display unit mirrors the movement simulated by the virtual dynamics model, making the original dynamics of the display unit transparent to the operator. The execution of Step 404 may drive the display unit in a direction following the operator's head movement, thus reducing an existing offset between the point of contact and the head input device. A detailed description of the steps that may be used to drive the display unit is provided below with reference to FIG. 8.

Turning to FIGS. 5A and 5B, interactions of the operator's head with a headrest of a display unit, in accordance with one or more embodiments, are shown. FIG. 5A provides a side view of the interaction, whereas FIG. 5B provides a top view or the interaction.

Turning to FIG. 5A, the operator's head (570) and torso (572) are shown.

In the interaction (500), the operator's head (570) is in contact with the headrest (510) at a point of contact (530). In one or more embodiments, the headrest sensor (520), interfacing with the headrest (510), is configured to sense forces and/or torques caused by the interaction of the operator's head (570) with the headrest (510). In one embodiment, the headrest sensor includes sensory modalities for forces exerted in multiple directions and torques exerted in multiple direction. FIG. 5A shows a Cartesian coordinate system (548) establishing a reference frame with respect to ground. When viewed in conjunction with the operator (head (570), torso (572)), the x-direction may be understood as representing a left/right shift of the operator's head, the y-direction may be understood as representing a forward/backward shift of the operator's head, and the z-direction may be understood as representing an up/down shift of the operator's head. A rotation about the x-direction may be understood as a pitch movement, and a rotation about the z-direction may be understood as a yaw movement of the operator's head. The sensing of the headrest sensor (520) may also be performed in a Cartesian reference frame in up to six degrees of freedom (three translational and three rotational). The headrest sensor, in some embodiments, may be a sensor that provides measurements in fewer translational and/or rotational degrees of freedom, such as only forces in the x-direction, y-direction and z-direction, and only torques about the x-direction and the z-direction. The degrees of freedom of the headrest sensor are not necessarily aligned with the reference frame established by the coordinate system (548). In the example of FIG. 5A, the headrest sensor (520) has a pivotal offset about the x-direction. Accordingly, in the example of FIG. 5A, the headrest sensor obtains a force approximately corresponding to an in/out movement, $F_{I/O}$ (544), a force approximately corresponding to an up/down movement, $F_{U/D}$ (542), and a torque, $\tau_x$ (540). Conversions between different reference frames may be performed at any time using trigonometric operations. In particular, $F_y$ (538) and $F_z$ (536), which are in the ground-based Cartesian reference frame, may be directly computed based on the combination of $F_{I/O}$ (544) and $F_{U/D}$ (542).

In the illustration of FIG. 5A, shows an offset (546). While the offset is shown between the point of contact (530) and the headrest sensor (520), in a real-world scenario an offset may exist between the instantaneous point of contact (530) and an initial point of contact (not shown). The offset may be a result of the operator's head movement, causing the point of contact (530) to move away from the initial point of contact. Because the subsequently described methods cause movement of the display unit (206) to compensate for the offset (546), the offset may be temporary.

In one or more embodiments, the headrest (510) has a known geometry. Accordingly, the offset (546) in a vertical y-z plane may be directly estimated using force/torque equilibrium equations. In the example of FIG. 5A, $F_{I/O}$ (544), $F_{U/D}$ (542), $\tau_x$ (540) are available to determine the offset (546).

For illustrative purposes, the offset between the point of contact and the headrest center (or an original point of contact), as shown in FIG. 5A is significant. When executing the subsequently described methods, the actual encountered offset is likely to be considerably smaller because the methods drive a compensatory movement that reduces the offset.

Turning to FIG. 5B, the scenario initially shown in FIG. 5A is shown as a top view. Accordingly, various elements introduced in FIG. 5A have corresponding elements in FIG. 5B. In the interaction (500), the operator's head (570) is in contact with the headrest (510) at a point of contact (530). In the example of FIG. 5B, the headrest sensor registers forces in a y-direction, $F_y$ (584), approximately corresponding to an in/out shift of the operator's head. The headrest sensor further registers forces in an x-direction, $F_x$ (582), approximately corresponding to a left/right shift of the operator's head. In addition, the headrest sensor registers torques about a z-direction, $\tau_z$ (590), approximately corresponding to a yaw motion of the operator's head. Although, in FIG. 5B, the degrees of freedom of the headrest sensor are shown as aligned with the reference frame established by the coordinate system (548), the sensing degrees of freedom of the headrest sensor may alternatively be in a reference frame that has a rotational offset relative to the reference frame established by the coordinate system (548), for example, when the display unit (206) of FIG. 2, including the headrest sensor (520), has a yaw offset. Standard trigonometric operations may be used to convert between the reference frames.

When installed on the display unit (206) of FIG. 2A and FIG. 2B, the headrest may be centered above the viewports (223). In the illustration of FIG. 3, an offset between the point of contact (330) and the headrest sensor (320) exists. While the offset is shown between the point of contact (530) and the headrest sensor (520), in a real-world scenario, and offset may exist between the instantaneous point of contact (530) and an initial point of contact (not shown). The initial point of contact is not necessarily aligned with the headrest sensor (520). The offset may be a result of the operator's head movement. Because the subsequently described methods cause movement of the display unit (206) to compensate for the offset, the offset may be temporary.

In one or more embodiments, the headrest (510) has a known curvature. Accordingly, whenever the operator's head (570) is not aligned with the headrest center of the initial point of contact, an offset in an x-direction, $x_{offset}$ (552) and in the y-direction, $y_{offset}$ (554), may exist. The force, F (580), applied by the operator's head (570), thus, results in the equilibrium equation $$x_{offset}F_y - y_{offset}F_x = \tau_z,$$

with $F_x$ (582), $F_y$ (584) representing the components of force F (580) in x and y directions, respectively, and with $\tau_z$ (590) being the opposing torque. With measurements for $F_x$ (582), $F_y$ (584), and $\tau_z$ (590) being provided by the headrest sensor (520), and a known relationship between $x_{offset}$ and $y_{offset}$ based on the known curvature of the headrest, the point of contact (530) in a horizontal x-y plane may be determined.

While the above description discusses offsets for the headrest configuration shown in FIG. 5A and FIG. 5B, offsets may also be calculated for headrests with different geometries, head sensors that are placed differently, etc., without departing from the disclosure. Those skilled in the art will appreciate that the calculation of offsets involves force-torque equilibrium equations that may be adapted based on the configuration being used. Different configurations may necessitate different trigonometric operations and/or force-torque equilibrium equations.

FIG. 5B further shows a computed shear force, $F_{shear}$ (586), and a computed normal force, $F_{normal}$ (588), which are later used to control the movement of the display unit (206). $F_{shear}$ (586) is parallel to the surface of the headrest (510) at the point of contact (530), whereas $F_{normal}$ (588) is perpendicular to the surface of the headrest (510) at the point of contact (530). $F_{shear}$ and $F_{normal}$ and may be computed for surfaces of any shape.

For illustrative, non-limiting purposes, the offset between the point of contact and the headrest center (or the initial point of contact), as shown in FIG. 5B is significant. When executing the subsequently described methods, the actual encountered offset is likely to be considerably smaller because the methods drive a compensatory movement that reduces the offset.

Figure 6:
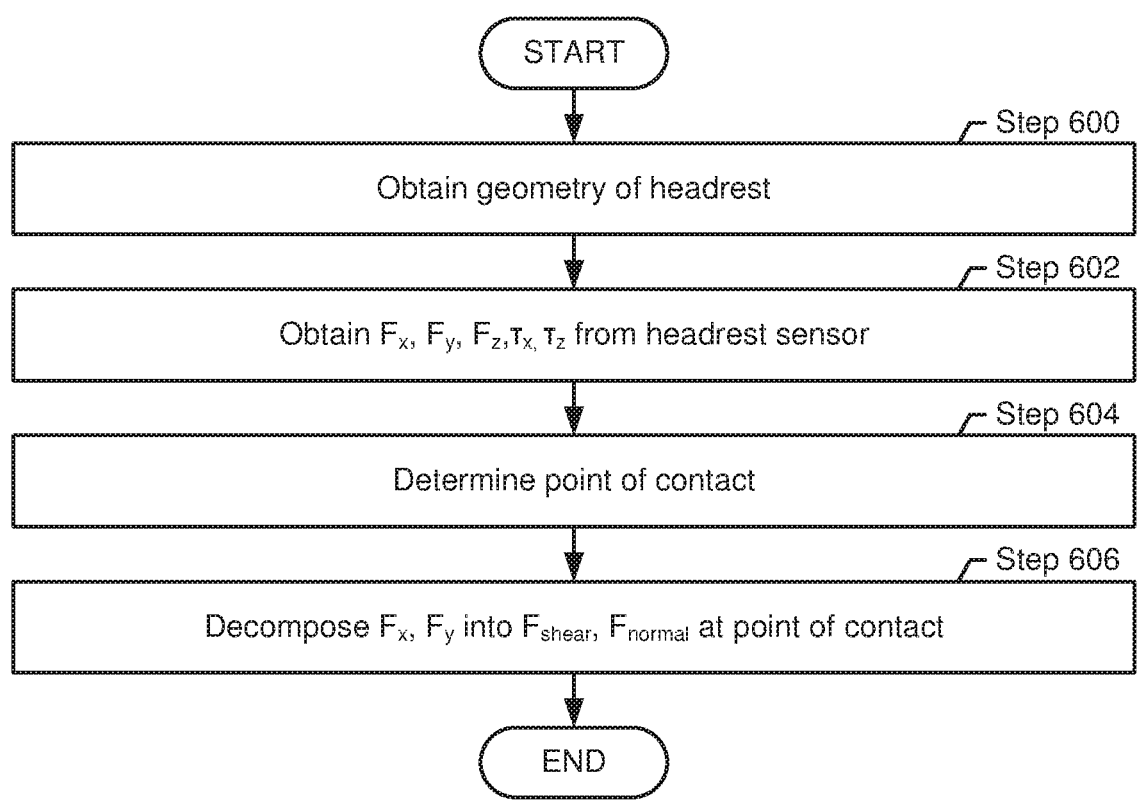
FIG. 6 shows a flowchart describing methods for sensing mechanical input by the operator's head, in accordance with one or more embodiments.

Turning to the flowchart of FIG. 6, a method for obtaining sensor signals reflecting the operator's head movements, in accordance with one or more embodiments, is shown. The method may be used to register the operator's head movements in a substantially horizontal plane. The method may also be used to register the operator's head movement in a substantially vertical plane.

In Step 600, the geometry of the headrest is obtained. The headrest in the x/y-plane (i.e., in a horizontal plane, as previously illustrated in FIG. 5B) may be curved. The headrest in the y/z-plane (i.e., in a vertical plane, as previously illustrated in FIG. 5A) may be straight of substantially straight. The geometry of the headset may be stored in the form of a headrest model, for example, a polygonal headrest model. In one embodiment of the disclosure, a polygonal headrest model that is smoothed using cubic splines is used. Any other model that establishes a relationship between x and y coordinates (in the horizontal plane), and between y and z coordinates (in the vertical plane) of the headrest may be used without departing from the disclosure.

In Step 602, sensor signals are obtained from the headrest sensor. In one embodiment of the disclosure, the obtained sensor signals include at least sensor signals representing $F_x$, $F_y$, $F_z$, $\tau_x$, and $\tau_z$. Other sensor signals may be obtained without departing from the disclosure. While the originally obtained sensor signals may be in a headrest sensor-specific reference frame, the sensor signals may be converted to any other reference frame using trigonometric operations, based on a known current position and/or orientation of the headrest sensor.

The sensor signals may be obtained in any format (e.g., as a digital or analog reading), and may be converted into a format enabling the readout of the measured forces/torques corresponding to the actual forces/torques encountered by the headrest sensor.

In Step 604, the location of the point of contact between the head and the headrest is determined, in accordance with one or more embodiments. The point of contact may be obtained in the vertical plane (as illustrated in FIG. 5A) and/or in the horizontal plane (as illustrated in FIG. 5B). In the example configuration shown in FIG. 5B, the point of contact in the horizontal plane may be determined using the relationship $x_{offset}F_y - y_{offset}F_x = \tau_z$. $x_{offset}$ and $y_{offset}$ may be used to describe the location of the point of contact relative to the headrest sensor. Because the relationship between x and y coordinates is known due to the previously obtained geometry of the headrest, the equation may be solved for $x_{offset}$ and $y_{offset}$, using the sensor signals obtained for $F_x$, $F_y$, and $\tau_z$. In one embodiment of the disclosure, $x_{offset}$ and $y_{offset}$ describe the location of the point of contact relative to the center of the headrest which may or may not correspond with the location of the headrest sensor. In the example configuration shown in FIG. 5A, the point of contact in the vertical plane may be determined in a similar manner. However, in the vertical plane, the point of contact may be obtained relative to an initially recorded point of contact (e.g., when the operator's head initially contacted the headrest) which does not necessarily correspond to the location of the headrest sensor. As a result, a perfect alignment between the operator's head and the center of the headrest or the headrest sensor is unnecessary.

In Step 606, $F_x$ and $F_y$ are decomposed into a normal force, $F_{normal}$, and a shear force, $F_{shear}$, in accordance with one or more embodiments. The execution of Step 606 is specific to the horizontal plane, illustrated in FIG. 5B. No shear force and normal force may be calculated in the vertical plane, illustrated in FIG. 5A. The decomposition may be performed based on the known geometry of the headrest at the point of contact using trigonometric operations. Specifically, a tangential direction is obtained for $F_{shear}$ at the point of contact, and subsequently the magnitudes of $F_{shear}$ and $F_{normal}$ are determined. $F_x$, $F_y$, $F_{normal}$, and $F_{shear}$ are shown in FIG. 5B. $F_{normal}$ and $F_{shear}$ may subsequently be used for the simulated driving of the virtual dynamics model.

While not shown in the flowchart of FIG. 6, a sanity check may be performed on the obtained sensor signals. For example, the sensor signals may only be accepted if the corresponding force is pointing in a direction that is physically meaningful. A direction of a force may not be meaningful, for example, if the direction is toward the operator, thus suggesting a pulling rather than a pushing force. Similarly, a direction of a force may not be meaningful if $F_{shear}$ is excessive relative to $F_{normal}$. At least a minimum $F_{normal}$ is typically necessary to allow a certain level of $F_{shear}$ without the operator's head slipping on the headrest. If physically implausible sensor signals are detected, they may be ignored. In addition or alternatively, the operator may receive a visual or auditory warning.

After execution of the method of FIG. 6, the force and torque components for simulatively driving a virtual dynamics model are available.

Figure 7:
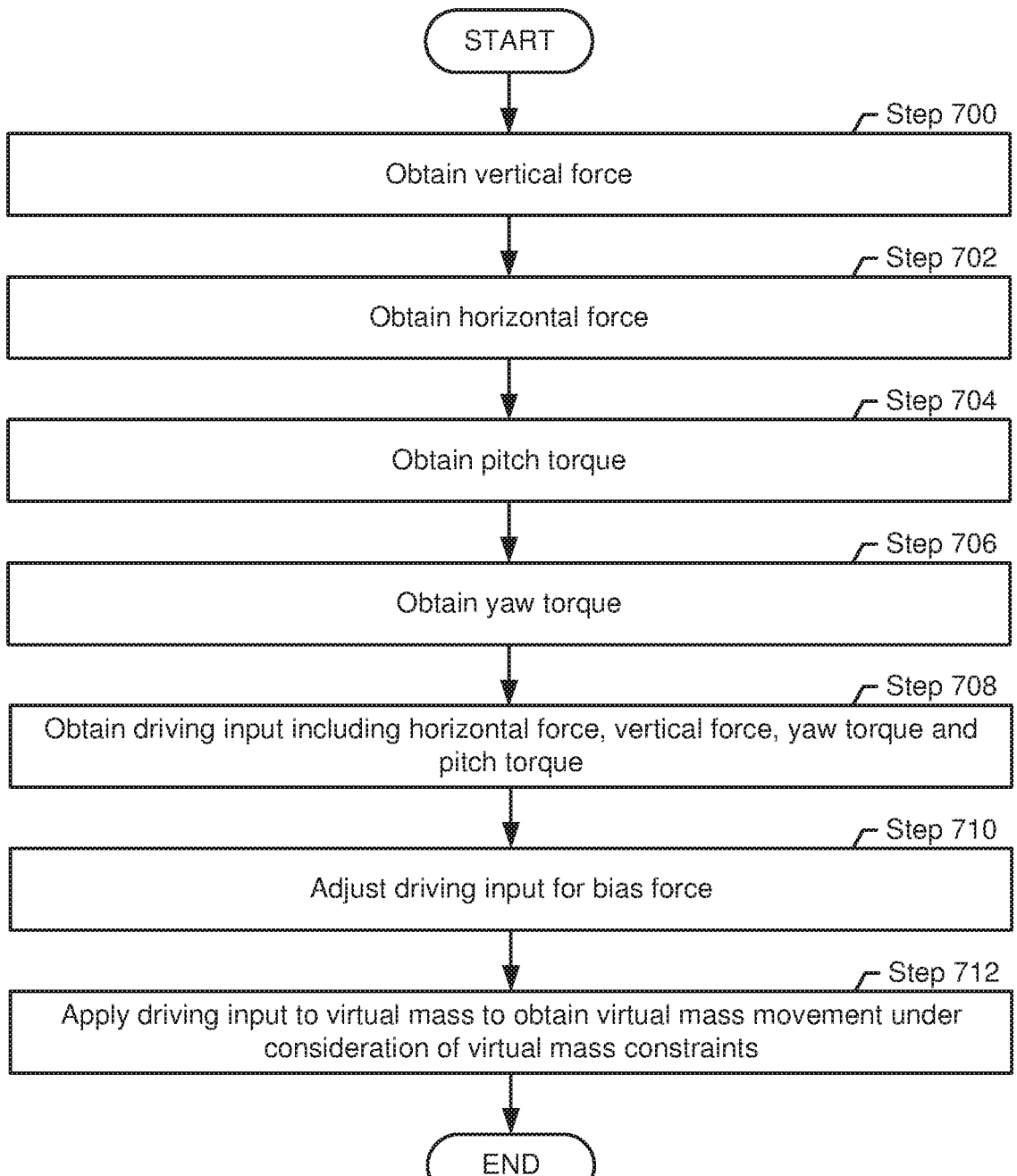
FIG. 7 shows a flowchart describing a method for simulating movement using a virtual dynamics model, driven by the sensed mechanical input, in accordance with one or more embodiments.

Turning to the flowchart of FIG. 7, a method for simulating movement of a virtual dynamics model, in accordance with one or more embodiments, is shown. The virtual dynamics model may be driven using the sensed mechanical input obtained as described in FIG. 6.

In Step 700, a vertical force is obtained. The vertical force may be the $F_z$ shown in FIG. 5A. $F_z$ may be in a ground-based Cartesian reference frame. As previously noted, $F_z$ may be directly obtained from the forces reported by the headrest sensor using trigonometric operations, when the headrest sensor is not aligned with the ground-based Cartesian reference frame.

In Step 702, a horizontal force is obtained. The horizontal force may be the $F_y$ shown in FIG. 5A. $F_y$ may be in a ground-based Cartesian reference frame. As previously noted, $F_y$ may be directly obtained from the forces reported by the headrest sensor using trigonometric operations, when the headrest sensor is not aligned with the ground-based Cartesian reference frame. Alternatively, $F_y$ may be obtained as shown in FIG. 5B.

In Step 704, a pitch torque is obtained. The pitch torque may be obtained using the distance between the current point of contact (in the same or a similar fashion as obtained in Step 604) and an initial point of contact. The distance may be multiplied by a pitch coefficient or gain. The initial point of contact may be obtained at one point in time, for example, when the operator initially activates the control of the steerable display unit by head movement. The obtained pitch torque may be about the center of the headrest and may be oriented to drive the display unit and the headrest in a direction resulting in the current point of contact being closer to the initial point of contact. As a result, the display unit and the headrest may follow the operator's head movement, as further discussed in detail below.

In Step 706, a yaw torque is obtained. Analogous to the pitch torque, the yaw torque may be oriented to drive the display unit and the headrest in a direction that gets the current point of contact closer to the center of the headrest. The obtained yaw torque may be about an axis that passes through the center of a physical or virtual yaw joint, for example, as shown in FIG. 2. The yaw torque may include an additive combination of two terms. The first term may be a point of contact term, and the second term may be a shear force term.

The point of contact term may be obtained using the distance between the current point of contact (as obtained in Step 604) and the center of the headrest (which may or may not coincide with the location of the headrest sensor). The distance may be multiplied by a yaw coefficient or gain. The coefficient may be tunable to allow adjustment of the effect of the distance.

The point of contact term may be particularly beneficial for detecting head movement that includes a "rolling" motion of the operator's head in the head rest because the rolling changes the point of contact. More specifically, a rolling head motion directly results in a shift of the point of contact.

The shear force term may be obtained as follows: referring to FIG. 5B, the shear force term may be obtained by derating $F_{shear}$ using $F_{normal}$. The derating may scale $F_{shear}$ in a manner to provide a smaller horizontal force when $F_{normal}$ is elevated while providing a larger horizontal force when $F_{normal}$ is reduced. The derating may be performed multiplicatively (e.g., by multiplication of $F_{shear}$ with the inverse of $F_{normal}$) and using a tunable gain to allow scaling the effect of the derating. The derating may enable the operator to more accurately control movement of the viewing system. Specifically, when an operator is heavily leaning against the headrest, producing a high $F_{normal}$, $F_{shear}$ may also be elevated because when producing a high $F_{normal}$, the operator's ability to finely control $F_{shear}$ may be limited. In contrast, the operator may have good control over $F_{shear}$ when only lightly touching the headrest. The derating may further address potential stability issues in the control loop: A higher $F_{normal}$ effectively increases the stiffness of the overall closed-loop control system. If the control loop gain (for a control using $F_{shear}$ as an input) is optimized for a lower $F_{normal}$, i.e., based on a less stiff mechanical system, the direct use of $F_{shear}$ may result in an instability when controlling the higher-stiffness mechanical system resulting from the increased $F_{normal}$, thereby potentially causing oscillations. The derating of $F_{shear}$ ensures that the overall closed-loop control system remains within a stable region.

The derated $F_{shear}$ may be multiplied by a radius to obtain the shear force term. The radius may be the distance between the point of contact and the center of a physical or virtual yaw joint, for example, as shown in FIG. 2. The shear force term may be particularly beneficial for detecting a head movement that includes a pivoting of the head (yaw) because the pivoting causes a shear force.

In Step 708, a driving input is obtained by vectorially combining the horizontal force, the vertical force, the yaw torque and the pitch torque. The driving input, thus, provides a four-dimensional, directional force-torque to be used for simulatively driving the virtual dynamics model.

In Step 710, the driving input is adjusted for a bias force. The bias force may be perpendicular to the surface of the headrest, at the center of the headrest, pointing toward the operator. The bias force may be applied to keep contact with the operator's head. In other words, the bias force causes the headrest to produce a force against the operator's head. The bias force may be selected to provide sufficient friction between the operator's head and the headrest to enable the operator to transmit forces and/or torques to the headrest when performing head movements. In addition, when the operator withdraws the head, the bias force causes the headrest to follow the operator's head. The bias force may be constant or be progressive, i.e., increasing with insertion, thereby requiring progressively more force to be applied by the operator's head when advancing in the insertion direction. Although the bias force may be in a direction perpendicular to the headrest, the horizontal and vertical forces of the driving input may be adjusted to introduce the bias force. The horizontal and vertical force adjustment may be computed based on the current orientation of the headrest.

In Step 712 the driving input is simulatively applied to the virtual dynamics model. In one or more embodiments, the virtual dynamics model includes a virtual mass. The virtual mass may be configurable to adjust the inertia of the simulated system. A velocity-dependent damping may act on the virtual mass. Further, friction, e.g., coulomb friction, may be included in the virtual dynamics. The forces and torques represented by the driving input may act on the virtual mass causing an acceleration of the virtual mass. Accordingly, at any point in time, the virtual mass may move in a virtual space, based on the inputs driving the virtual mass.

In one or more embodiments, the virtual dynamics model has additional characteristics. For example, the virtual mass may be constrained to a limited virtual space. The limitations of the virtual space may be derived from physical workspace constraints of the imaging device and/or the display unit. By constraining the virtual space not to exceed the physical workspace, it may be ensured that when the display unit is driven to follow the virtual dynamics model (as described below), the physical workspace boundaries are not reached or exceeded. Limits to the virtual space may be introduced by reducing the velocity of the virtual mass as a boundary is approached. The velocity reduction may be gradual, until a zero velocity is reached at the boundary. The constraints of the virtual space may be static or dynamic. Static constraints of the virtual workspace may reflect physical workspace constraints. Dynamic constraints of the virtual workspace may be set and adjusted based on spontaneously occurring events such as, for example, a predicted or actually occurring detected collision of the imaging device being controlled.

In the above description, the virtual mass is primarily driven by the operator's head movement. Additional factors may affect the simulated movement of the virtual mass. In one embodiment of the disclosure, haptic events may be rendered by altering the dynamics of the virtual mass. These haptics events may implement virtual control elements such as switches which may be implemented through simulation of rigid or compliant surfaces, springs with configurable stiffnesses, etc. The haptic events may be introduced through modulation of the driving input, in Step 708. A haptic event may be introduced by additively modulating the driving input. Because movement of the display unit may mirror movement of the simulated virtual mass, the operator may physically experience the haptic event.

A haptic event may be position-dependent. For example, a virtual switch may be implemented based on the current location of the display unit, allowing the virtual switch to be placed, for example, at the border of the physically available workspace. The current location of the display unit may be obtained using position sensors (e.g., encoders of the actuators driving the linkage of the display unit). Forward kinematics may be used to obtain the current location in a reference frame suitable for defining a location of the haptic event. A haptic event may be mapped to other features of the robotic system. For example, hitting a virtual wall at the border of the available workspace may start the recording of a video, activate a particular tool, switch between different operating modes, etc.

Figure 8:
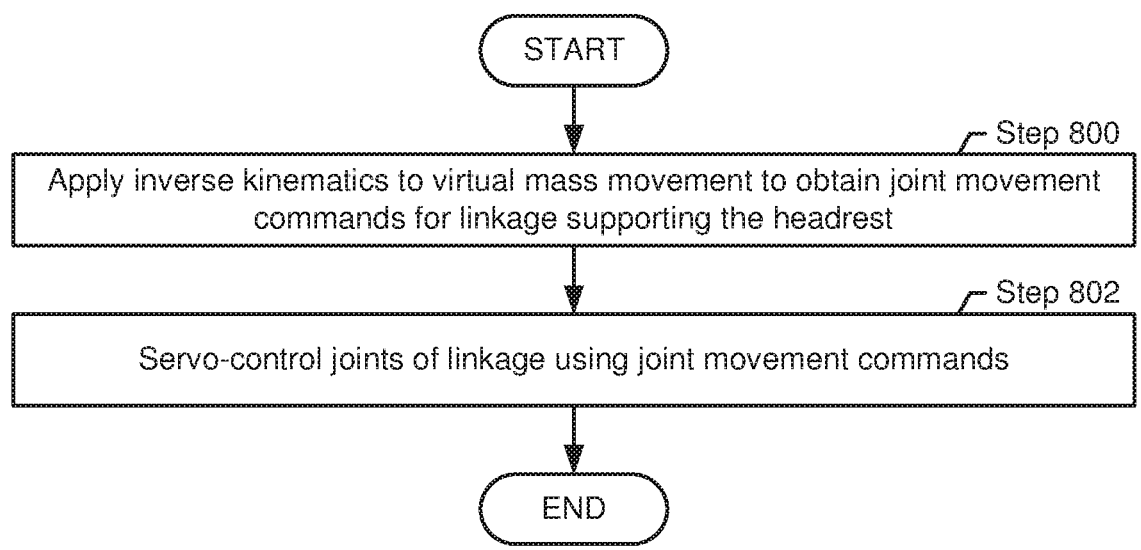
FIG. 8 shows a flowchart describing a method for causing movement of the headrest of the display unit to follow the movement produced by the virtual dynamics model, in accordance with one or more embodiments.

Turning to the flowchart of FIG. 8, a method for causing movement of the display unit and the headrest attached to the display unit, in accordance with one or more embodiments, is shown. The method of FIG. 8 may cause the headrest to follow the simulated movement of the virtual dynamics model. Alternatively, in one embodiment, the headrest is directly driven using the driving input. In this case, no virtual dynamics model may be necessary.

In Step 800, an inverse kinematics model of the linkage supporting the display unit and the headrest is operating on the velocity of the virtual mass to generate joint movement commands for the actuators driving the joints of the linkage. The inverse kinematics model may, thus, be used to drive the joints of the linkage supporting display unit and headrest such that the headrest or another point on the display unit accurately follows the virtual mass. The inverse kinematics model may be implemented, for example, using an inverse (or pseudo-inverse) Jacobian of the linkage supporting the display unit. While the output of the inverse kinematics model may be joint velocities, an integration may be performed to obtain commanded joint positions.

In Step 802, the joints of the linkage are driven using the joint movement commands. The joint movement commands may be position or velocity commands, depending on the servo controllers controlling the joints. A position-velocity-time (PVT) interpolation may be used for joint movement commands provided as positions.

With the completion of Step 802, the display unit may be moving in a direction based on the operator's head movement to reach a state in which the display unit is aligned with the operator's head. Further, movement of the imaging system may be caused in response to determination of the movement of the operator's head or of the display unit, and update the view provided to the operator. As a result, head movement enables the operator to control the view obtained from the imaging device, while the compensatory movement of the display unit ensures that the display unit remains in alignment with the operator's head to provide a proper viewing configuration without misalignment between the operator's eyes and the viewports of the display unit. At times, the imaging device may be decoupled from the operator's head movement. The benefit may be that, during the decoupling, the view provided by the imaging device may remain stable even in presence of small naturally occurring shaking or other "jiggling" head movements of the operator. The decoupling may be accomplished through the implementation of an input dead-band. The input dead-band may be implemented by ignoring force/torque inputs below a set threshold, whenever the operator stops moving. The dead-may be established around the location at which the operator stopped moving. The dead-band may be deactivated as soon as the operator applies force/torque inputs above the threshold.

Because the dynamics of the compensatory movement, in accordance with one or more embodiments, are governed by a virtual dynamics model which may be configurable based on operator preferences, accuracy requirements, etc., the operator may receive the desired feedback experience, regardless of the original dynamics of the display unit. As long as the inverse kinematics model accurately represents the display unit and the linkage supporting the display unit, the display unit may accurately follow the simulated movement of the virtual mass, thereby superseding the original dynamics with the desired dynamics.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A computer-assisted robotic system comprising:
   a display unit configured to provide images to an operator of the display unit;
   a headrest configured to receive a mechanical input provided by a head of the operator in mechanical contact with the headrest;
   a headrest sensor interfacing with the headrest and configured to provide sensor signals based on the mechanical input;
   a controller comprising a computer processor, the controller configured to:
   process the sensor signals to obtain a driving input;
   drive, by the driving input, a virtual mass to obtain a simulated virtual mass movement; and
   cause movement of the headrest, the movement of the headrest tracking the virtual mass movement.

2. The computer-assisted robotic system of claim 1, wherein the headrest is disposed on the display unit, and
   wherein a linkage supporting the display unit enables the movement of the headrest in conjunction with movement of the display unit, and
   wherein the linkage comprises a plurality of joints.

3. The computer-assisted robotic system of claim 2,
   wherein the display unit comprises a viewport configured to display the images, and
   wherein the controller is configured to, using the driving input, maintain an alignment of the viewport with the head during a head movement that causes the mechanical input to the headrest.

4. The computer-assisted robotic system of claim 1, wherein processing the sensor signals to obtain the driving input comprises determining a point of contact between the head and the headrest.

5. The computer-assisted robotic system of claim 4, wherein determining the point of contact comprises: using an equilibrium of forces and torques and a geometry of the headrest, wherein the forces and torques are represented by the sensor signals.

6. The computer-assisted robotic system of claim 1, wherein processing the sensor signals to obtain the driving input comprises determining a shear force at a point of contact between the head and the headrest.

7. The computer-assisted robotic system of claim 6, wherein processing the sensor signals further comprises derating the shear force based on a normal force at the point of contact.

8. The computer-assisted robotic system of claim 1, wherein the driving input obtained from processing the sensor signals comprises a horizontal force, a vertical force, a yaw torque, and a pitch torque.

9. The computer-assisted robotic system of claim 1, wherein the controller is further configured to:
   adjust the driving input to include a bias force.

10. The computer-assisted robotic system of claim 9, wherein: the bias force acts perpendicularly to a surface of the headrest, at a center of the headrest, and oriented toward the head; or the bias force biases a horizontal force and a vertical force of the driving input.

11. The computer-assisted robotic system of claim 1, wherein driving the virtual mass comprises: simulating a friction or simulating a damping.

12. The computer-assisted robotic system of claim 1, wherein the controller is further configured to render a haptic event by altering the driving input or a dynamics of the virtual mass according to the haptic event.

13. The computer-assisted robotic system of claim 1, further comprising an imaging device,
   wherein the imaging device is configured to provide the images, and
   wherein the controller is further configured to control a movement of the imaging device based on the mechanical input.

14. A method for operating a robotic system, comprising:
    obtaining sensor signals from a headrest sensor,
      wherein the headrest sensor interfaces with a headrest configured to receive a mechanical input provided by a head of an operator, the head being in mechanical contact with the headrest, and
      wherein the sensor signals are based on the mechanical input;
    processing the sensor signals to obtain a driving input;
    driving, by the driving input, a virtual mass to obtain a simulated virtual mass movement; and
    causing movement of the headrest, the movement of the headrest tracking the virtual mass movement.

15. The method of claim 14, wherein the headrest is disposed on a display unit, and wherein a linkage supporting the display unit enables the movement of the headrest in conjunction with movement of the display unit, the method further comprising:

using the driving input to maintain an alignment of viewports of the display unit with the head during a head movement that causes the mechanical input to the headrest.

16. The method of claim 14, wherein processing the sensor signals to obtain the driving input comprises determining a point of contact between the head and the headrest.

17. The method of claim 16, wherein the point of contact is determined using an equilibrium of forces and torques and a geometry of the headrest, the forces and torques represented by the sensor signals.

18. The method of claim 14, wherein processing the sensor signals to obtain the driving input comprises determining a shear force at a point of contact between the head and the headrest.

19. The method of claim 18, wherein processing the sensor signals further comprises derating the shear force based on a normal force at the point of contact.

20. The method of claim 14, further comprising:
adjusting the driving input to include a bias force, wherein:
the bias force acts perpendicularly to a surface of the headrest, at a center of the headrest, and oriented toward the head, or the bias force biases a horizontal force and a vertical force of the driving input.

21. The method of claim 14, further comprising:
rendering a haptic event by altering the driving input or a dynamics of the virtual mass according to the haptic event.

22. A non-transitory machine-readable medium comprising a plurality of machine-readable instructions executed by one or more processors associated with a medical system, the plurality of machine-readable instructions causing the one or more processors to perform a method comprising:
obtaining sensor signals from a headrest sensor,
wherein the headrest sensor interfaces with a headrest configured to receive a mechanical input provided by a head of an operator, the head being in mechanical contact with the headrest, and
wherein the sensor signals are based on the mechanical input;
processing the sensor signals to obtain a driving input;
driving, by the driving input, a virtual mass to obtain a simulated virtual mass movement; and
causing movement of the headrest, the movement of the headrest tracking the virtual mass movement.

23. The non-transitory machine-readable medium of claim 22, wherein processing the sensor signals to obtain the driving input comprises determining a point of contact between the head and the headrest.

24. The non-transitory machine-readable medium of claim 22, wherein processing the sensor signals to obtain the driving input comprises determining a shear force at a point of contact between the head and the headrest.

* * * * *